United States Patent
Jayaraman et al.

(10) Patent No.: US 10,282,959 B2
(45) Date of Patent: May 7, 2019

(54) FATIGUE TIME DETERMINATION FOR AN ACTIVITY

(71) Applicant: TATA CONSULTANCY SERVICES LIMITED, Mumbai, Maharashtrai (IN)

(72) Inventors: Srinivasan Jayaraman, Karnataka (IN); Balamuralidhar Purushothaman, Karnataka (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 430 days.

(21) Appl. No.: 13/716,800

(22) Filed: Dec. 17, 2012

(65) Prior Publication Data

US 2013/0159041 A1 Jun. 20, 2013

(30) Foreign Application Priority Data

Dec. 17, 2011 (IN) .......................... 3550/MUM/2011

(51) Int. Cl.
*G08B 21/02* (2006.01)
*A61B 5/18* (2006.01)
(Continued)

(52) U.S. Cl.
CPC ............ *G08B 21/02* (2013.01); *A61B 5/0022* (2013.01); *A61B 5/18* (2013.01); *G06F 19/00* (2013.01); *G06Q 10/06314* (2013.01); *G06Q 10/063114* (2013.01); *G08B 21/06* (2013.01); *G16H 40/67* (2018.01); *A61B 5/0402* (2013.01);
(Continued)

(58) Field of Classification Search
CPC ................................................ G06F 2203/011
See application file for complete search history.

(56) References Cited

U.S. PATENT DOCUMENTS

| 4,502,122 A | * | 2/1985 | Yanagishima | ......... G08B 21/06 180/272 |
|---|---|---|---|---|
| 4,612,655 A | | 9/1986 | Nakamura | |

(Continued)

FOREIGN PATENT DOCUMENTS

| DE | 10324841 | 6/2003 |
|---|---|---|
| EP | 0334224 | 3/1989 |

(Continued)

OTHER PUBLICATIONS

Driving Fatigue and Performance among Occupation Drivers in Simulated Prolonged Driving; Global Journal of Health and Science; SzeSeen Kee et al; Apr. 2010 (Year: 2010).*

(Continued)

*Primary Examiner* — Deirdre D Hatcher
(74) *Attorney, Agent, or Firm* — Lee & Hayes, P.C.

(57) ABSTRACT

Systems and methods for determining an actual fatigue time (AFT) for an activity are provided. The method comprises receiving a standard fatigue time (SFT) representing a time duration. The SFT is indicative of an onset of fatigue in individuals upon continuously performing the activity. The method further comprises receiving at least one external parameter and a fatigue index corresponding to the at least one external parameter. The at least one external parameter and the fatigue index are associated with the activity. The method further comprises determining the AFT for the activity based upon the SFT and the fatigue index.

12 Claims, 3 Drawing Sheets

(51) Int. Cl.
- *G08B 21/06* (2006.01)
- *G06Q 10/06* (2012.01)
- *A61B 5/00* (2006.01)
- *G06F 19/00* (2018.01)
- *G16H 40/67* (2018.01)
- *A61B 5/0402* (2006.01)
- *A61B 5/0476* (2006.01)
- *A61B 5/0488* (2006.01)
- *A61B 5/11* (2006.01)

(52) U.S. Cl.
CPC .......... *A61B 5/0476* (2013.01); *A61B 5/0488* (2013.01); *A61B 5/1112* (2013.01); *A61B 5/7257* (2013.01); *Y04S 10/54* (2013.01)

(56) References Cited

U.S. PATENT DOCUMENTS

| | | | |
|---|---|---|---|
| 5,850,193 A * | 12/1998 | Shimoura et al. | 340/995.1 |
| 2003/0095046 A1* | 5/2003 | Borugian | 340/576 |
| 2004/0046666 A1* | 3/2004 | Yasuchi | 340/573.1 |
| 2009/0070163 A1* | 3/2009 | Angell et al. | 705/7 |
| 2009/0153598 A1 | 6/2009 | Blank et al. | |
| 2010/0219955 A1 | 9/2010 | Demirdjian et al. | |
| 2011/0109462 A1 | 5/2011 | Deng et al. | |

FOREIGN PATENT DOCUMENTS

| | | |
|---|---|---|
| EP | 2508125 | 10/2012 |
| WO | WO2011/111056 | 9/2011 |

OTHER PUBLICATIONS

EP Search Report dated Oct. 8, 2013 for EP 12197410, 18 pages.

Goldstein M J et al, Work Hours Assessment and Monitoring Initiative (WHAMI) under resident direction: A strategy for working within limitations, Current Surgery. Wiliams and Wilkins, Baltimore, US, vol. 62, No. 1, Jan. 1, 2005.

Johnm Irvine and Steven A Israel, A Sequential Procedure for Individual Identity Verification Using ECG, EURASIP Journal on Advances in Signal Processing, Hindawi Publishing Corp. US, vol. 2009.

Regulation (EC) No. 561/2006 of the European Parliament and of the Council of Mar. 15, 2006 on the harmonisation of certain social legislation relating to road transport and amending Council Regulations (EEC) No. 3821/85 and (EC) No. 2135/98 and repealing Council Regulation (EEC) No. 3820/85, Official Journal of the European Union, European Union, Luxembourg Apr. 11, 2006.

Tackling Fatigue: EU Social Rules and Heavy Goods Vehicle Drivers, Praise: Preventing Road Accidents and Injuries for the Safety of Employees, No. 7, Oct. 1, 2011.

\* cited by examiner

US 10,282,959 B2

FATIGUE TIME DETERMINATION FOR AN ACTIVITY

TECHNICAL FIELD

The present subject matter described herein, in general, relates to systems and methods for determining fatigue time for an activity.

BACKGROUND

People perform a gamut of activities such as driving a vehicle, working on a heavy machine, working as a labor at a construction site, working on a computer in an office, and the like. People may feel fatigued due to continuous performing of these activities. Fatigue is the effect of prolonged period of activity or an increasing disinclination to continue performing an activity in hand, accompanied by general and localized aches and pains, which depends on a nature and environment of the activity. Fatigue in a broad sense refers to a state that involves psychological (mental) and physical tiredness or exhaustion.

In one example, a driver of a vehicle may feel fatigued due to long driving hours. Driving involves low level of activation of muscles and a high level of concentration, thereby resulting in fatigue. Drivers of heavy vehicles, such as trucks, buses, and tankers are accustomed to driving for long durations and at irregular timings. However, not all drivers are accustomed to driving in such conditions and therefore feel fatigued. A task of driving demands persistent alertness failing which may result in severe consequences like road accidents.

A study by National Central University in Jhongli, Tatung University, Taiwan, recently reported in the New Scientist magazine that driving for just 80 minutes without a break can make drivers fatigued and therefore a danger on roads. The study states that drivers who do not take frequent rest stops have slower reactions than those who break up long journeys. The study further suggests that a break should be taken in every two hours of continuous driving.

Further, fatigue related vehicle crashes are often more severe than those caused due to other reasons. Fatigue delays drivers' reaction times and therefore fatigued drivers fail to make any maneuvers to avoid a crash. There are many factors that influence fatigue in drivers. These factors may include time of day, traffic conditions, climatic conditions, vehicle type and fitness, road conditions, and the like. Impact of fatigue causes a person to feel sleepy and this impact is much faster during night time than during day time. Also, long journeys on monotonous roads, such as highways, are the most likely to result in a driver falling asleep.

SUMMARY

This summary is provided to introduce concepts related to systems and methods for determining fatigue time for an activity and the concepts are further described below in the detailed description. This summary is not intended to identify essential features of the claimed subject matter nor is it intended for use in determining or limiting the scope of the claimed subject matter.

In one implementation, a method for determining an actual fatigue time (AFT) for an activity is provided. The method comprises receiving a standard fatigue time (SFT) representing a time duration. The SFT is indicative of an onset of fatigue in individuals upon continuously performing the activity. The method further comprises receiving at least one external parameter and a fatigue index corresponding to the at least one external parameter. The at least one external parameter and the fatigue index are associated with the activity. The method further comprises determining the AFT for the activity based upon the SFT and the fatigue index.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

System and method for determining actual fatigue time (AFT) for an activity are described herein. The AFT is representative of a time duration that a worker may spend on the activity at a stretch before the worker starts feeling fatigued. The AFT may be determined for a variety of activities such as driving, laboring, working on a computer, and the like. The AFT may vary for different activities and individuals as these are governed by different sets of external parameters.

Specifically, the AFT for a worker may be determined based upon a standard fatigue time (SFT) and a set of external parameters. The SFT is representative of a time duration and is indicative of an onset of fatigue in workers in general. For example, it is known in the art that labors working on a heavy machine generally get fatigued after one hour of continuous work. This one hour may be referred to as SFT for labors working on that particular machine. Though the SFT provides an estimate of the onset of fatigue upon continuously working on the machine, the estimate may not be accurate at all time. For example, different labors work under different conditions, i.e., they are exposed to different sets of external parameter and accordingly the SFT may not be same for all workers. For example, if a labor is working during day time at 25 degree Celsius in a congenial environment, then the labor may not get tired in one hour but in 1.5 hours. Similarly, if a labor is working during a hot summer day at 42 degree Celsius, then the labor may get tired within 45 minutes. Thus, the SFT needs to be modified based on external conditions to get an accurate estimate of the onset of fatigue. Therefore, it may be understood that AFT may be determined based upon the set of external parameters and the SFT.

The AFT may be used to generate a work schedule for a worker. In one example, the work schedule may suggest an on-time duration and an off-time duration for a worker engaged in the activity. The on-time may be indicate the time duration for which the activity may be performed continuously without experiencing fatigue and off-time may indicate the time duration for which the work may take a break from the activity. The worker may or may not comply with the work schedule. If the worker does not comply with the work schedule, an alert may be generated.

Referring to the foregoing example, if the labor working on the heavy machine has been working continuously for a long duration, this may result in fatal accidents if the labor is fatigued and also quality of work may get reduced. The work schedule notifies the labor that a break needs to be observed. In case of non-compliance with the work schedule, stakeholders, such as a manger of the labor may be alerted thus avoiding unwanted consequences.

Figure 1:
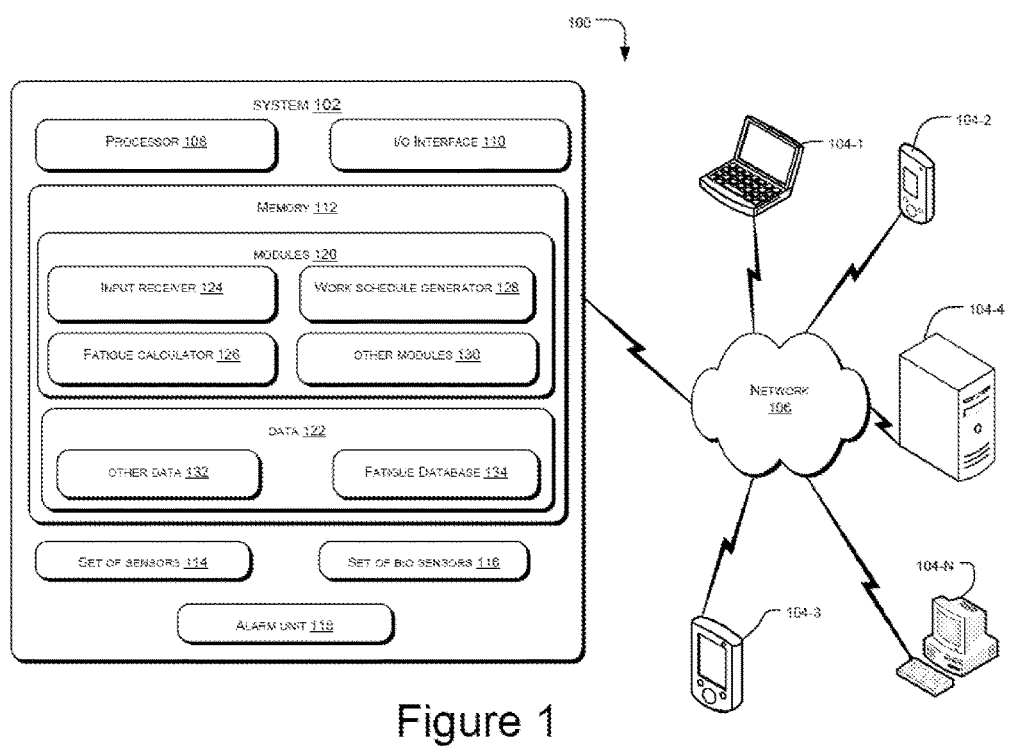
FIG. 1 illustrates a network implementation of a system for determining an actual fatigue time (AFT) for an activity, in accordance with an embodiment of the present subject matter.

Referring now to FIG. 1, a network implementation 100 of a system 102 for determining an actual fatigue time (AFT) for an activity is illustrated, in accordance with an embodiment of the present subject matter. Further, the system 102 may be implemented in a variety of computing systems. The system 102 may be accessed through one or more external devices 104-1, 104-2, . . . 104-N, collectively referred to as external devices 104 hereinafter, or applications residing on the external devices 104. Examples of the external devices 104 may include, but are not limited to, a portable computer, a personal digital assistant, a handheld device, and a workstation. In one implementation, the external devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

In one embodiment, the system 102 may include at least one processor 108, an I/O interface 110, a memory 112, a set of sensors 114, a set of bio sensors 116, and an alarm unit 118. Although in the present embodiment, the set of sensors 114, the set of bio sensors 116, and the alarm unit 118 are shown to be inside the system 102; however, in another embodiment, the set of sensors 114, the set of bio sensors 116, and the alarm unit 118 may reside outside the system 102 and may be functionally coupled to the system 102.

In the present embodiment, the at least one processor 108 may be implemented as one or more microprocessors, microcomputers, microcontrollers, digital signal processors, central processing units, state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with a user directly or through the external devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 112 may include modules 120 and data 122.

The modules 120 include routines, programs, objects, components, data structures, etc., which perform particular tasks or implement particular abstract data types. In one implementation, the modules 120 may include an input receiver 124, a fatigue calculator 126, a work schedule generator 128, and other modules 130. The other modules 130 may include programs or coded instructions that supplement applications and functions of the system 102.

The data 122, amongst other things, serves as a repository for storing data processed, received, and generated by one or more of the modules 120. The data 122 may also include other data 132 and a fatigue database 134. The other data 132 may include data generated as a result of the execution of one or more modules in the other module 130.

In one embodiment, the system 102 helps in determining an actual fatigue time (AFT) for an activity. Examples of the activity may include driving a vehicle, working on a heavy machine, working as a labor at a construction site, working on a computer in an office, and the like. The present subject matter may be explained considering the activity to be driving; however, it will be appreciated by a person skilled in the art that the activity may be any other physical and/or mental activity for which an AFT may be calculated using the method and the system 102 described herein.

Considering, in one example, the activity to be driving a vehicle, in one embodiment, the system 102 may be a portable device that may be installed in the vehicle, for example, on the dashboard or the steering wheel of the vehicle. In various other embodiments, the system 102 may be integrated with other onboard devices, such as a GPS device installed in the vehicle. Further, in one embodiment, the system 102 may be a portable device, such as a mobile communication device. In said implementation, the system 102 may be a mobile phone configured to determining an actual fatigue time (AFT) for driving. It will be appreciated that the system 102 may have various implementation depending on the activity for which the system 102 may be employed. The present example that considers driving as the activity should not be construed as a limitation. The concepts explained in relation thereto may be extended to other activities, albeit few modifications that will be apparent to one skilled in the art.

Figure 2:
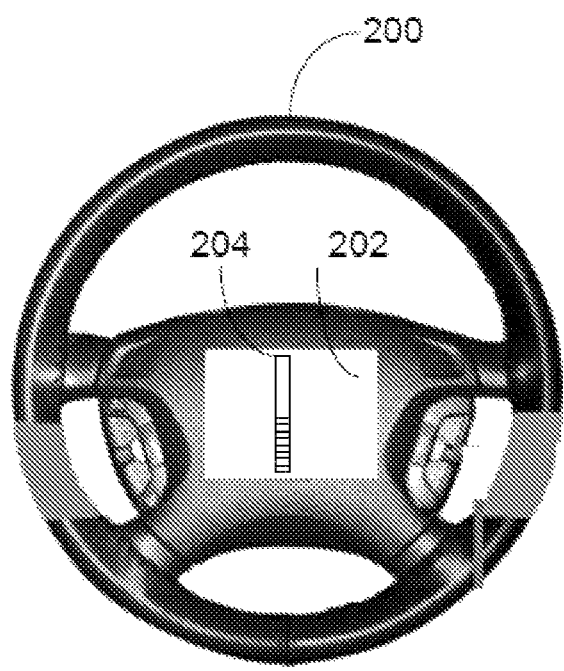
FIG. 2 shows a steering wheel of a vehicle fitted with the system of FIG. 1, in accordance with an embodiment of the present subject matter.

In one implementation, the system 102 of FIG. 1 may be integrated into a steering wheel 200, shown in FIG. 2, of a vehicle, such as a car, a bus, and a truck. In order to better understand the subject matter, FIG. 1 and FIG. 2 may be explained in conjunction.

Referring to FIG. 1, the system 102 may include several modules for determining the AFT for the activity, i.e., driving. For example, in case where the activity is driving a vehicle, the AFT is representative of a time duration that a driver may spend on driving at a stretch before the driver starts feeling fatigued. As mentioned above, the AFT may be determined based upon a standard fatigue time (SFT) and a set of external parameters. As will be apparent, the AFT for a given activity is based on the SFT for the activity and the external parameters associated with the activity.

In one implementation, the SFT for driving may be determined by conducting an experiment. In this experiment, a plurality of drivers may be asked to drive on a plurality of routes for several hours continuously. After a few hours of driving, the drivers may start feeling fatigued. The time duration at which drivers start feeling fatigued may be determined. In one example, an onset of fatigue in the drivers may be determined by measuring a change in the set of biological parameters. Based upon the change in the biological parameters, the onset of fatigue of the drivers may be determined. The set of biological parameters may include an inclination of driver's head, a sagging posture of the driver, a decline in gripping force on a steering wheel of the vehicle, a decline in eye activity, and the like. The changes may be determined either by appropriate sensors or by human supervision of the driver.

Subsequently, the SFT may be calculated by taking an average of time durations when the plurality of drivers start feeling fatigued. Based on the experiment, it may be determined that SFT for driving a car is 120 minutes and SFT for driving a truck is 80 minutes. The SFT may therefore be indicative of an onset of fatigue in drivers in general. In the present implementation, the SFT is determined by monitoring a set of biological signals for each of the plurality of drivers. Specifically, a change in the set of biological signals is measured to determine an onset of fatigue, i.e., the SFT. In one example, the set of biological signals may include an Electrocardiogram (ECG) signal, an Electroencephalogram (EEG) signal, an Electromyography (EMG) signal, a hand pressure signal, and a seat pressure signal. In another embodiment, data regarding the SFT for various activities may already be known and available, for example, in an empirical data repository, and may be obtained therefrom.

As mentioned above, the set of external parameters associated with the activity is also taken into consideration for determining the AFT. This is because the set of external parameters may alter the SFT for the activity. In one example, when the activity involves operating a heavy machine, the set of external parameters may include a machine condition, a machine type, a climatic condition, and a time of a day. In another example, when the activity involves driving, the set of external parameters may include a road type, a road condition, a vehicle type, a vehicle condition, a terrain, a climatic condition, a time of a day, and a traffic condition. As may be understood, the AFT may vary for drivers susceptible to varying external parameters. For example, an AFT for a driver who is driving a luxury car on a wide traffic free express way on a bright sunny day may be different from a driver who is driving a truck on a mountainous terrain on a rainy day. Therefore, it may be understood that the set of external parameters may alter SFT for different drivers subject to different external parameters.

In one implementation, each of the external parameters mentioned above may further be classified into various sub categories. For example, road type may be classified into four sub categories, namely, national highway, state highway, city road, and rural road. Similarly, road condition may be classified into three sub categories, namely, bad, good, and excellent. A fatigue index is associated with each of the sub categories for each of the external parameter. For example, a fatigue index for national highway may be defined as 0.9, a fatigue index for state highway may be 0.95, and a fatigue index for city road may be 1.0. Table 1 shown below summarizes each of the set of external parameters and a plurality of fatigue indexes associated with the external parameters. Table 1 may be stored in the fatigue database 134. Although in the present embodiment the fatigue database 134 is shown to be inside the system 102, in another embodiment, the fatigue database 134 may be outside the system 102.

TABLE 1

The set of external parameters and corresponding fatigue indexes

| Road Type | National Highway (0.9) | State highway (0.95) | City Road (1.0) | Rural road (1.2) |
|---|---|---|---|---|
| Road Condition | Bad (1.2) | Good (1.0) | Excellent (0.95) | |
| Vehicle Type | Car (1.0) | Bus (1.1) | Truck (1.2) | Tractor (1.3) |
| Vehicle Condition | Bad (1.1) | Good (1) | Excellent (0.95) | |
| Terrain | Plains (1.0) | Hilly (1.2) | | |
| Climatic Condition | Rainy (1.2) | Foggy (1.3) | Hot Summer (1.15) | |
| Time of Day | Early Morning (1.3) | Day (1.0) | Evening (1.1) | Night (1.2) |
| Traffic Condition | Heavy (1.1) | Medium (1.0) | Low (0.9) | |

In one embodiment, the fatigue indexes shown in Table 1 may be calculated by performing certain experiments with drivers driving under various external parameters defined above. In one example, a driver driving a truck on a high way during the day time is observed to be free of fatigue till about 80 minutes and the driver may start feeling fatigued after continuously driving for more than 80 minutes. In the present example, the SFT is 80 minutes and an observed fatigue time (OFT), that is when the driver starts feeling fatigued, is also 80 minutes. The observed fatigue time is indicative of onset of fatigue observed in the driver. In the present example, the fatigue index for the day time is $$\frac{SFT}{OFT}$$

which is 80/80=1.0. In another example, the same driver may drive the same vehicle at a night time under identical conditions. The observed fatigue time (OFT) for night driving may come out to be 65 minutes, i.e., the driver may start feeling fatigued after 66 minutes during night time. Therefore, fatigue index for night time is $$\frac{SFT}{OFT}$$

which is 80/65=1.2. Similarly, fatigue indexes may be determined for each of the set of external parameters. In another embodiment, fatigue indexes may be determined by calculating relative alpha activities by means of integrated power spectral data and normalized with area under curve 0.5-26 Hz during driving and replay modes using Fast Fourier Transform (FFT).

Although Table 1 shows the set of external parameters and corresponding fatigue indexes for driving, it may be understood that fatigue indexes may also be computed in a same way for other activities, such as for operating a heavy machine and working on a computer.

In one implementation, an AFT for a driver may be calculated using a following formula:

$$AFT = SFT * F_d * \left( \prod_{i=1}^{n} \frac{1}{F_i} \right) \quad (1)$$

Where, $F_d$ is a driver specific fatigue factor based on a biological condition of the driver, and $F_i$ is a fatigue index due to the external parameters associated with a driver, $F_i$ may be fetched from Table 1. In one implementation, $F_d$ may be dependent upon personal characteristics of the driver. The personal characteristics may include health, age, and the like. $F_d$ may be determined in a way similar to the calculation of $F_i$ as described above.

In one example, the formula described above may be used to calculate AFT for a driver who is planning a trip from X location to Y location in a truck. In this example, at first, as the driver holds the steering wheel 200 of the truck, the set of bio sensors 116 may monitor a biological signal of the driver. The biological signal may be used to identify the driver. In one example, the set of bio sensors 116 may include at least one of an Electrocardiogram (ECG) sensor, an Electroencephalogram (EEG) sensor, and an Electromyography (EMG) sensor. Subsequently, the driver may input the set of external parameters using the I/O interface 110 of the system 102. In one example, the set of external parameters for a driver may be:

Road type: National highway
Road condition: Good
Vehicle type: Truck
Vehicle condition: Good
Terrain: Plains
Climatic condition: Rainy
Time of a day: Day
Traffic condition: Medium In the present implementation, the set of external parameters are input by the driver. However, in other embodiments, a subset of the external parameters may be determined by the set of sensors 114 or may be obtained from one or more external sources, such as from the external devices 104. Examples of the external source may include various service providers that provide real time information relating to weather and traffic condition for a given location. For example, the external device 104-4 may be a server maintained by a traffic surveillance service provider that may provide input relating to the traffic condition to the system 102. In one more example, the external device 104-2 may be a smart phone of the driver that has a weather application installed on it. The weather application on the external device 104-2 may, on one hand, communicate with a cellular service provider to obtain updates on the weather and, on the other hand, communicate with the system 102 to provide 'climate condition' as input to the system 102. The external device 104-2 and the system 102 may be communicatively coupled through means, such as Bluetooth®.

Further, examples of the set of sensors 114 that provide external parameters to the system 102 may include climate sensors (not shown), such as a temperature sensor, a rain sensor, a fog detector, and a humidity sensor fitted on the vehicle. The climate sensors may determine and send the respective 'climate condition' related information to the input receiver 124. The input receiver 124 may fetch a fatigue index corresponding to the climate condition from Table 1. For example, if climate sensors detect that it is rainy day, then the climate sensors may indicate the input receiver 124 about the rainy day. Based on the climate condition, the input receiver 124 may fetch a fatigue index corresponding to the rainy day, i.e., 1.2.

Further, the set of sensors 114 may include a steering wheel movement sensor (not shown). The steering wheel movement sensor may determine an angle of rotation of the steering wheel 200 and a frequency of rotation of the steering wheel 200 of a vehicle. Based upon the angle of rotation of the steering wheel 200, a 'traffic condition' may be determined; and based upon the frequency of rotation of the steering wheel 200, a 'terrain' may be determined. Information related to 'traffic condition' and 'terrain' may be sent to the input receiver 124. The input receiver 124 may fetch corresponding fatigue indexes from Table 1.

The external parameters that may be either manually input by the driver or may be received by the set of sensors 114 and/or the external source are received by the input receiver 124 of the system 102. Subsequently, the system 102 may use the fatigue calculator 126 to calculate the AFT for the driver based on the external parameters received by the input receiver 124.

Based upon the external parameters received by the input receiver 124 and the corresponding fatigue indexes, the fatigue calculator 126 may calculate AFT for the driver, in accordance with equation (1):

AFT=120*1/0.9*1/1*1/1.2*1/1*1/1*1/1.2*1/1*1/1=92.6 minutes

In the above example, it may be seen that although the SFT is 120 minutes, the set of external parameters alter the SFT to give rise to AFT for the driver based upon the set of external parameters applicable to the driver.

In one embodiment, based upon the AFT, a real time fatigue index (RTFI) may be generated by the fatigue calculator 126 of the system 102. The RTFI is an indicative of a degree of fatigue in the driver in a real time. In one example, the RTFI may be in form of a bar 204 that may keep on increasing as a driving duration of the driver is approaching the AFT. The RTFI may be displayed on a display screen 202 of the steering wheel 200. The display screen 202 may display an estimate safe driving duration, i.e., time remaining from the AFT. In the present example, the AFT for the driver is 96 minutes. As the driver starts driving, the bar 204 representing RTFI may have a lowest height representing a lowest degree of fatigue. However, as a driving times passes, the height of the bar 204 keeps on increasing suggesting an increase of fatigue in the driver. As will be understood, in other embodiments, a display for the RTFI may be included in the system 102 or on any part of the vehicle, for example, the dashboard of the vehicle.

Further, based on the AFT, the work schedule generator 128 may generate a work schedule for the driver. The work schedule may be indicative of an on-time duration of driving and an off-time duration of driving for the driver. The on-time may be indicate the time duration for which the driver may drive the vehicle continuously without experiencing fatigue and off-time may indicate the time duration for which the driver may be required to take a break from driving. In the present example, the AFT for the driver came out to be 96 minutes. The work schedule may suggest the driver to drive for a maximum of 96 minutes at a stretch and then take a break. Thus, the on-time in this example is 96 minutes. If the driver has to travel for several hours together, then the driver may take a break from driving after every 96 minutes and, in accordance with one embodiment, the off-time may suggest the duration of the break. For example, at the start of a journey, when the driver is rather fresh, the work schedule may include shorter off-time duration, however, after the driver has been driving for a significantly long duration, he may be suggested to observe longer breaks, i.e., off-time duration.

The driver may or may not follow the work schedule generated by the work schedule generator 128. Therefore, compliance of the driver with the work schedule may be monitored. In order to monitor such compliance, the duration for which a driver has continuously been driving is monitored. In addition, an identity of the driver also needs to be established. For example, in case there are more than one driver taking turns to drive the vehicle, the compliance of the work schedule is based on the identification of the drivers and the duration for which the identified driver has continuously been driving.

For the purpose, in one embodiment, the set of bio sensors 116 may be used to identify a driver. In one example, the driver is identified based on biological signals comprising an Electrocardiogram (ECG) signal, an Electroencephalogram (EEG) signal, an Electromyography (EMG) signal of the driver. In another example, biometric sensor may be installed to identify the driver based on the biometric data of the driver. The biometric data may include, for example, finger prints data, eye retina data, ECG, and face detection data.

Further, the system 102 also determines the duration for which the identified driver has continuously been driving with the help of the set of bio sensors 116. As the system 102, in the example considered above, is integrated in the steering wheel 200, the set of bio sensors 116 may be used to detect biological signals produced by the driver when at least one hand of the driver is on the steering wheel 200. However, if both the hands of the driver are not placed on the steering wheel 200, biological signal may not be detected by the set of bio sensors 116. Therefore, in one implementation, continuous reception of the biological signal of the driver along with signals from GPS or accelerometer is indicative of driving duration. However, absence of reception of the biological signal for more than a predetermined time may suggest that the driver has taken a break and is not driving anymore. In one example, the predetermined time may be 2 minutes.

In the present implementation, the set of bio sensors 116 are placed on a side bar of the steering wheel 200 so that the driver's hands, when placed on the steering wheel, touch the set of sensors 114. The biological signals generated by the driver have a low voltage of approximately 1 mV. Due to the low voltage, the biological signals are amplified using a differential amplifier. Subsequently, the biological signals are filtered to reject noise present in the biological signals and to collect predetermined frequencies from the biological signals. Thereafter, the biological signals are passed on to a digital section which includes a microcontroller and an Analogue to Digital Converter. The biological signal is then sampled at 250 Hz. The sampled biological signals are preprocessed and feature parameters are acquired and stored for future processing.

In the present implementation, a first driver may take a break from driving or may ask a second driver to drive after the driving time reaches AFT. Once the second driver sits on the steering wheel 200, the set of bio sensors 116 may identify the change and record that the first driver has taken a break. The record is used to determine compliance with the work schedule generated for the first driver. Further, the system 102 may, in parallel, also monitor the work schedule compliance for the second driver that may have been generated, for example, at the first instance the second driver took to the steering wheel, or, based on an input provided to the system 102, at the start of the journey.

In the present implementation, the set of bio sensors 116 is coupled to a counter timer (not shown). The counter timer is started as soon as the reception of biological signal is begun and is stopped when the biological signal is not received for a time period equal to the predetermined time. In the present example, if the reception of biological signals from either the first or from the second driver, as the case may be, is for more than 96 minutes, it may be assumed that the driver is not following the work schedule. In one embodiment, on non-compliance of the driver with the work schedule, the alarm unit 118 may generate an alert. However, in another embodiment, the driver may input a time period after which the alert may be generated by the alarm unit 118. Examples of the alert may include a Short Messaging Service (SMS), an audio signal, and a visual signal. The alert may indicate to a set of stakeholders associated with the vehicle that the driver is at an onset of fatigue and should take a break. The set of stakeholders may include the driver, other occupants of the vehicle, and an owner who is remotely located from the vehicle. For example, the alarm unit 118, may be configured to sent an alert, such as a SMS to the external device 104-3 belonging to an owner of the vehicle.

Therefore, the system 102 may be used to determine an AFT for an activity. The AFT may vary for different workers as they may be susceptible to different set of external parameters. Based upon the AFT, a work schedule may be generated. Further, compliance of more than one worker with the work schedule may be monitored. Furthermore, on non-compliance of the worker with the work schedule, an alert may be generated. Although, the present subject matter is explained considering the activity to be driving, it is to be understood that the system 102 may be used for determination AFT for any type of work, such as handling heavy machinery, and the like.

Figure 3:
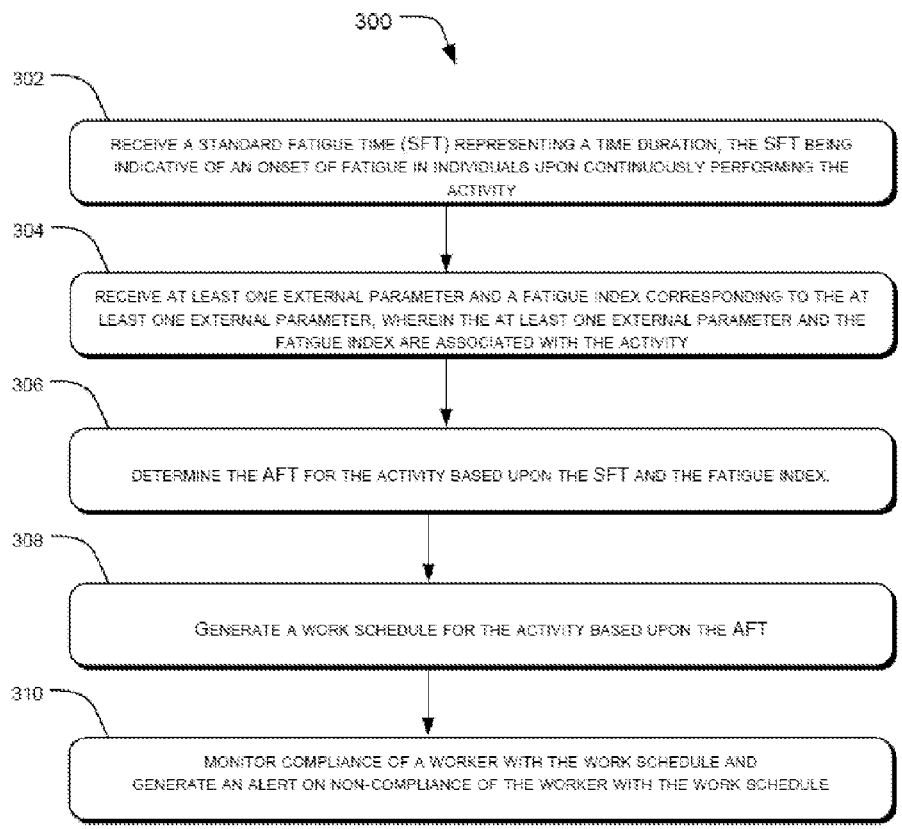
FIG. 3 shows a flowchart illustrating a method for determining an actual fatigue time (AFT) for an activity, in accordance with an embodiment of the present subject matter.

Referring now to FIG. 3, a method 300 for determining an actual fatigue time (AFT) for an activity is shown, in accordance with an embodiment of the present subject matter. The method 300 may be described in the general context of computer executable instructions. Generally, computer executable instructions can include routines, programs, objects, components, data structures, procedures, modules, functions, etc., that perform particular functions or implement particular abstract data types. The method 300 may also be practiced in a distributed computing environment where functions are performed by remote processing devices that are linked through a communications network. In a distributed computing environment, computer executable instructions may be located in both local and remote computer storage media, including memory storage devices.

The order in which the method 300 is described is not intended to be construed as a limitation, and any number of the described method blocks can be combined in any order to implement the method 300 or alternate methods. Additionally, individual blocks may be deleted from the method 300 without departing from the spirit and scope of the subject matter described herein. Furthermore, the method can be implemented in any suitable hardware, software, firmware, or combination thereof. However, for ease of explanation, in the embodiments described below, the method 300 may be considered to be implemented in the above described system 102.

At block 302, a standard fatigue time (SFT) representing a time duration is received. The SFT is indicative of an onset of fatigue in individuals upon continuously performing the activity. The SFT may either be determined by performing the experiment explained above or may be obtained from sources known in the art. In one example, the SFT is received by the input receiver 124.

At block 304, at least one external parameter and a fatigue index corresponding to the at least one external parameter is received. The at least one external parameter and the fatigue index are associated with the activity. In one example, the at least one external parameter is received by the input receiver 124.

At block 306, the AFT may be determined based upon the SFT and the at least one fatigue index. In one example, the AFT is determined by the fatigue calculator 126.

At block 308, a work schedule for the activity based upon the AFT may be generated. The work schedule comprises an on-time duration and an off-time duration for a worker engaged in the activity. In one example, the work schedule is generated by the work schedule generator 128.

At block 310, compliance of the worker with the work schedule may be monitored. Further, on non-compliance of the worker with the work schedule, an alert may be generated. In one example, the alarm unit 118 may generate the alert.

Although implementations for methods and systems for determining an actual fatigue time (AFT) for an activity have been described in language specific to structural features and/or methods, it is to be understood that the appended claims are not necessarily limited to the specific features or methods described. Rather, the specific features and methods are disclosed as examples of implementations for determining an actual fatigue time for an activity.

The invention claimed is:

1. A computer implemented method for determining an actual fatigue time (AFT) for a worker performing an activity, the method comprising:
   identifying, by a processor, the worker performing the activity based upon a set of biological parameters of the worker received from a set of bio sensors, wherein the activity is operating a heavy machine, wherein the set of biological parameters comprises at least one of a biological signal produced by the worker during the activity and biometric data of the worker;
   receiving a standard fatigue time (SFT) of the activity, by the processor, wherein the standard fatigue time is indicative of a time duration for an onset of fatigue in the worker upon continuously performing the activity, wherein the onset of fatigue in the worker is determined by measuring a change in the set of biological parameters;
   receiving, by the processor, a plurality of external parameters associated with the activity and applicable to the worker performing the activity by using a set of external sources, wherein the external parameters alter the SFT of the activity based on the worker and an external parameter from the plurality of external parameter, and wherein the external parameter is classified into one or more sub-categories, wherein each of the one or more sub-categories is associated with a fatigue index;
   and wherein the plurality of external parameters comprise at least one of a machine condition of the heavy machine, a machine type of the heavy machine, a climatic condition during the activity, and a time of a day during the activity;
   determining, by the processor, the actual fatigue time for the worker performing the activity based upon the standard fatigue time, a worker specific fatigue factor based on biological condition of the worker performing the activity, and the fatigue index associated with each of the sub-categories of the external parameters, wherein the actual fatigue time is representative of a time duration that the worker spends performing the activity continuously before feeling fatigued; and
   generating, by the processor, a real time fatigue index of the worker performing the activity based upon the actual fatigue time, wherein the real time fatigue index is indicative of a degree of fatigue in the worker in real time, and wherein the real time fatigue index is represented as an increasing bar that increases as the time duration of the worker approaches actual fatigue time.

2. The computer implemented method of claim 1, further comprising generating a work schedule for the activity based upon the actual fatigue time, wherein the work schedule comprises an on-time duration and an off-time duration for the worker performing the activity.

3. The computer implemented method of claim 2, further comprising:
   monitoring compliance of the worker with the work schedule; and
   generating an alert on non-compliance of the worker with the work schedule.

4. The computer implemented method of claim 1, wherein the activity is driving of a vehicle, and wherein the plurality of external parameters comprise at least one of a road type, a road condition, a vehicle type, a vehicle condition, a terrain, a climatic condition during an activity, a time of a day during the activity, and a traffic condition during the activity.

5. A computer implemented system for determining an actual fatigue time (AFT) for a worker performing an activity, the computer implemented system comprising:
   a processor; and
   a memory coupled to the processor, wherein the memory comprising:
      an input receiver to:
         receive a set of biological parameters from a set of biosensors coupled to the system;
         identify the worker performing the activity based on the set of biological parameters, wherein the activity is operating a heavy machine, wherein the set of biological parameters comprises at least one of a biological signal produced by the worker during the activity and biometric data of the worker; and
         receive a standard fatigue time (SFT) of the activity, wherein the standard fatigue time is indicative of a time duration for an onset of fatigue in the worker upon continuously performing the activity, wherein the onset of fatigue in workers is determined by measuring a change in the set of biological parameters; and
         receive a plurality of external parameters associated with the activity, and applicable to the worker performing the activity by using a set of external sources, wherein the external parameters alter the SFT of the activity based on the worker and an external parameter from the plurality of external parameter, and wherein the external parameter is classified into one or more sub-categories, wherein each of the one or more sub-categories is associated with a fatigue index wherein the plurality of external parameters comprise at least one of a machine condition of the heavy machine, a machine type of the heavy machine, a climatic condition during the activity, and a time of a day during the activity; and a fatigue calculator to:

determine the actual fatigue time for the worker performing the activity based on the standard fatigue time, a worker specific fatigue factor, and the fatigue index, wherein the actual fatigue time is representative of a time duration that the worker spends performing the activity continuously before feeling fatigued, and wherein the worker specific fatigue factor is based on one or more biological conditions of the worker performing the activity and the fatigue index associated with the plurality each of the sub-categories of the external parameters, wherein the actual fatigue time is representative of a time duration that the worker spends performing the activity continuously before feeling fatigued;

generate a real time fatigue index of the worker performing the activity based upon the actual fatigue time, wherein the real time fatigue index is indicative of a degree of fatigue in the worker in real time and wherein the real time fatigue index is represented as an increasing bar that increases as the time duration of the worker approaches actual fatigue time.

6. The computer implemented system of claim 5, wherein the fatigue calculator obtains the standard fatigue time for a fatigue database.

7. The computer implemented system of claim 5, wherein the input receiver receives plurality of external parameters from at least one of the worker performing the activity, a set of sensors coupled to the system, and an external source.

8. The computer implemented system of claim 5, further comprising a work schedule generator to generate a work schedule during the activity for the worker performing the activity based upon the actual fatigue time, wherein the work schedule is indicative of an on-time duration and an off-time duration for a worker performing the activity.

9. The computer implemented system of claim 8, further comprising an alarm unit to generate an alert in case of non-compliance with the work schedule, wherein the alert is provided to stakeholders associated with the activity.

10. The computer implemented system of claim 5, wherein the fatigue calculator determines a real time fatigue index of the worker performing the activity based upon the actual fatigue time, wherein the real time fatigue index is an indicative of a degree of fatigue in the worker in a real time.

11. A non-transitory computer-readable medium having embodied thereon a computer program for executing a method for determining an actual fatigue time (AFT) for a worker performing an activity, the method comprising:

identifying, by a processor, the worker performing the activity based upon a set of biological parameters of the worker received from a set of bio sensors, wherein the activity is operating a heavy machine, wherein the set of biological parameters comprises at least one of a biological signal produced by the worker during the activity and biometric data of the worker;

receiving a standard fatigue time (SFT) of the activity, by the processor, wherein the standard fatigue time is indicative of a time duration for an onset of fatigue in the worker upon continuously performing the activity, wherein the onset of fatigue in workers is determined by measuring a change in the set of biological parameters;

receiving, by the processor, a plurality of external parameters associated with the activity, and applicable to the worker performing the activity by using a set of external sources, wherein the external parameters alter the SFT of the activity based on the worker and an external parameter from the plurality of external parameter, and wherein the external parameter is classified into one or more sub-categories, wherein each of the one or more sub-categories is associated with a fatigue index, and wherein the plurality of external parameters comprise at least one of a machine condition of the heavy machine, a machine type of the heavy machine, a climatic condition during the activity, and a time of a day during the activity;

determining, by the processor, the actual fatigue time for the worker performing the activity based upon the standard fatigue time, a worker specific fatigue factor based on biological condition of the worker performing the activity, and the fatigue index associated with each of the sub-categories of the external parameter, wherein the actual fatigue time is representative of a time duration that the worker spends performing the activity continuously before feeling fatigued; and generating, by the processor, a real time fatigue index of the worker performing the activity based upon the actual fatigue time wherein the real time fatigue index is indicative of a degree of fatigue in the worker in real time and wherein the real time fatigue index is represented as an increasing bar that increases as the time duration of the worker approaches actual fatigue time.

12. The computer implemented method of claim 1, wherein the biological parameters comprise a biological signal and biometric data of the worker, wherein the biological signal comprises at least one of an Electrocardiogram (ECG) signal, an Electroencephalogram (EEG) signal, an Electromyography (EMG) signal, and wherein the biometric data comprises at least one of finger prints data, eye retina data, ECG, and face detection data.

* * * * *